United States Patent
Zaiki (10) Patent No.: US 8,229,066 B2
(45) Date of Patent: Jul. 24, 2012

(54) X-RAY IMAGE DIAGNOSIS APPARATUS AND X-RAY IMAGE PROCESSING METHOD

(75) Inventor: Ryuji Zaiki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 274 days.

(21) Appl. No.: 12/695,704

(22) Filed: Jan. 28, 2010

(65) Prior Publication Data
US 2010/0202585 A1    Aug. 12, 2010

(30) Foreign Application Priority Data
Feb. 6, 2009 (JP) ................... 2009-025842

(51) Int. Cl.
*A61B 6/00* (2006.01)
(52) U.S. Cl. ............... 378/62; 378/95; 378/98.12
(58) Field of Classification Search ............... 378/8, 62, 378/95, 98.12; 600/428; 382/130, 132
See application file for complete search history.

(56) References Cited

U.S. PATENT DOCUMENTS
| | | | |
|---|---|---|---|
| 2003/0158476 A1* | 8/2003 | Takabayashi et al. | ........ 600/420 |
| 2007/0030946 A1 | 2/2007 | Tsuyuki et al. | |
| 2007/0140535 A1* | 6/2007 | Li et al. | ................. 382/128 |
| 2007/0280407 A1 | 12/2007 | Kunze et al. | |
| 2010/0128838 A1* | 5/2010 | Ayala et al. | ............... 378/4 |

FOREIGN PATENT DOCUMENTS
| | | |
|---|---|---|
| CN | 1907227 A | 2/2007 |
| CN | 101082991 A | 12/2007 |
| JP | 2006-34952 | 2/2006 |
| JP | 2007-244865 | 9/2007 |
| JP | 2008-61763 | 3/2008 |

OTHER PUBLICATIONS

Office Action issued Apr. 8, 2011, in Chinese Patent Application No. 201010104077.5 with English translation.

* cited by examiner

*Primary Examiner* — Glen Kao
(74) *Attorney, Agent, or Firm* — Oblon, Spivak, McClelland, Maier & Neustadt, L.L.P.

(57) ABSTRACT

An X-ray image diagnosis apparatus includes: an imaging unit that includes an X-ray generation unit and an X-ray detection unit, which are supported so as to be opposed to each other and rotatable about the body axis of a subject placed; a control unit that performs imaging for obtaining images within a predetermined angular range required for image reconstruction, the control unit rotating the imaging unit within a first angular range to perform a first imaging operation and then rotating the imaging unit within a second angular range to perform a second imaging operation such that a part of the first angular range and a part of the second angular range are overlapped with each other; and an image data processing unit that performs image reconstruction processing after compensating a displacement occurring between the images obtained by the first and second imaging operations.

6 Claims, 7 Drawing Sheets

IMAGING FOR OBTAINING CONTRAST IMAGE

IMAGING FOR OBTAINING MASK IMAGE

X-RAY IMAGE DIAGNOSIS APPARATUS AND X-RAY IMAGE PROCESSING METHOD

CROSS-REFERENCE TO RELATED APPLICATION

This application is based upon and claims the benefit of priority from the prior Japanese Patent Application No. 2009-25842, filed on Feb. 6, 2009, the entire contents of which are incorporated herein by reference.

BACKGROUND OF THE INVENTION

1. Field of the Invention

The present invention relates to an X-ray image diagnosis apparatus and an X-ray image processing method which are suitable for diagnosis of blood flow in capillaries.

2. Description of the Related Art

Conventionally, during endovascular treatment for cardiovascular disease, plaque may erupt to clog capillaries. To prevent this, an X-ray CT apparatus or angiographic apparatus is used to confirm the blood flow in the capillary phase after the treatment.

Further, in cardiovascular examination, in order to minutely observe the condition of blood vessels, a method has been employed in which mask image data obtained through imaging performed before injection of contrast medium into vessels and contrast image data obtained through imaging performed after injection of the contrast medium are subjected to subtraction to obtain a subtraction image emphasizing a contrast area as a diagnosis image.

Jpn. Pat. Appln. Laid-Open Publication No. 2008-61763 discloses an example of an X-ray image diagnosis apparatus capable of obtaining the subtraction image by applying subtraction to the mask image and contrast image.

When contrast medium is injected into an artery in angiographic examination, blood containing contrast medium flows from the artery to capillaries and further to the vein, with the result that the contrast medium is absorbed into body parts while the blood containing contrast medium passes through the body parts.

There has been proposed a brain perfusion technique using an X-ray CT apparatus in order to extract the capillary phase. In the brain perfusion technique, the contrast medium is injected through the vein for CT radioscopy, and time-density curve concerning an image is calculated to thereby derive a blood flow index.

The X-ray CT apparatus can make extraction of only the capillary phase. However, imaging needs to be performed after recovery of a patient, that is, imaging is performed several hours after treatment. Further, in the case where clogging of the vessel is found, the patient needs to be transferred to an examination room once again. Thus, extraction of the capillary phase in the X-ray CT apparatus involves time constraint and transfer.

Although the capillary phase can be extracted by a 3D-angiography technique using an angiographic apparatus, extraction of only the capillary phase is difficult to be achieved, and the obtained 3D image may include arterial and venous phases. That is, although 3D imaging using the angiographic apparatus can be performed immediately after treatment, a reconstructed image may include many artifacts. Further, at imaging time, an imaging unit (X-ray generator and X-ray detector) need to be rotated in an angle range of about 200 degrees.

Jpn. Pat. Appln. Laid-Open Publication No. 2006-34952 discloses an X-ray image diagnosis apparatus that applies subtraction to an X-ray image (mask image) that does not contain a figure of the contrast medium and an X-ray image (contrast image) that contains a figure of the contrast medium to generate image data corresponding to a differential image between the mask and contrast images and thereby clearly displays the flow of the contrast medium. More specifically, in the example of Jpn. Pat. Appln. Laid-Open Publication No. 2006-34952, a C-arm holding an X-ray tube and an X-ray detector is rotated around a subject by 200 degrees to perform imaging for generation of the mask image and then the C-arm is rotated around a subject by 200 degrees once again to perform imaging for generation of the contrast image.

Further, Jpn. Pat. Appln. Laid-Open Publication No. 2007-244865 discloses a display method that images the arterial and venous phases of the blood vessel system and displays them in a three-dimensional manner. More specifically, in the example of Jpn. Pat. Appln. Laid-Open Publication No. 2007-244865, imaging for obtaining the mask image is performed without use of contrast medium and imaging for obtaining the contrast image is performed a plurality of times with use of the contrast medium. In the imaging using the contrast medium, injection operation of the contrast medium is performed during the arterial phase and venous phase, respectively.

However, the time elapsed for blood containing contrast medium to flow into the capillaries through the artery is very short, so that a blood vessel image targeting only the capillary phase includes the arterial and venous phases, with the result that a reconstructed image may includes many artifacts. Further, if a subject moves during imaging for obtaining the contrast image, a displacement may occur between images obtained at the first and second imaging times.

SUMMARY OF THE INVENTION

An object of the present invention is to provide an X-ray image diagnosis apparatus and an X-ray image processing method capable of correctly generating a 3D image of the capillary phase.

According to a first aspect of the present invention, there is provided an X-ray image diagnosis apparatus comprising: an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed; a control unit that rotates the imaging unit about the body axis of the subject to perform imaging for obtaining images within a predetermined angular range required for image reconstruction, the control unit rotating the imaging unit within a first angular range to perform a first imaging operation and then rotating the imaging unit within a second angular range to perform a second imaging operation such that a part of the first angular range and a part of the second angular range are overlapped with each other; and an image data processing unit that performs image reconstruction processing based on images obtained through the first and second imaging operations after compensating a displacement occurring between the images obtained by the first and second imaging operations.

According to a second aspect of the present invention, there is provided an X-ray image diagnosis apparatus comprising: an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed; a control unit that rotates, after injection of contrast medium into the subject, the imaging unit about the body axis of the subject to perform imaging for obtaining images within a predetermined angular range required for image reconstruction, the control unit rotating the imaging unit within a first angular range to perform a first imaging operation and then rotating the imaging unit within a second angular range to perform a second imaging operation such that a part of the first angular range and a part of the second angular range are overlapped with each other; a timing setting unit that analyzes the time length from the injection of the contrast medium to the time at which blood containing the contrast medium reaches the capillaries based on the result of the first imaging operation and sets the X-ray irradiation start time in the second imaging operation based on the analysis result; and an image data processing unit that performs image reconstruction processing based on images obtained through the first and second imaging operations.

According to a third aspect of the present invention, there is provided an X-ray image processing method comprising: providing an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed; rotating the imaging unit within a first angular range to perform a first imaging operation at imaging time in which the imaging unit is rotated about the body axis of the subject to perform imaging for obtaining images within a predetermined angular range required for image reconstruction; rotating the imaging unit within a second angular range to perform a second imaging operation such that a part of the first angular range and a part of the second angular range are overlapped with each other; and performing image reconstruction processing after compensating a displacement occurring between the images obtained by the first and second imaging operations.

According to a fourth aspect of the present invention, there is provided an X-ray image processing method comprising: providing an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed; rotating the imaging unit within a first angular range after injection of contrast medium into the subject to perform a first imaging operation at imaging time in which the imaging unit is rotated about the body axis of the subject to perform imaging for obtaining images within a predetermined angular range required for image reconstruction; analyzing the time length from the injection of the contrast medium to the time at which blood containing the contrast medium reaches the capillaries based on the result of the first imaging operation; setting the X-ray irradiation start time in the second imaging operation based on the analysis result; rotating the imaging unit within a second angular range after injection of contrast medium into the subject to perform a second imaging operation such that a part of the first angular range and a part of the second angular range are overlapped with each other; and performing image reconstruction processing based on images obtained through the first and second imaging operations.

DETAILED DESCRIPTION OF THE INVENTION

Throughout this description, the embodiments and examples shown should be considered as exemplars, rather than limitations on the apparatus of the present invention.

Hereinafter, an embodiment of the present invention will be described in detail with reference to the accompanying drawings. Throughout the drawings, the same or similar elements are denoted by the same reference numerals.

Figure 1:
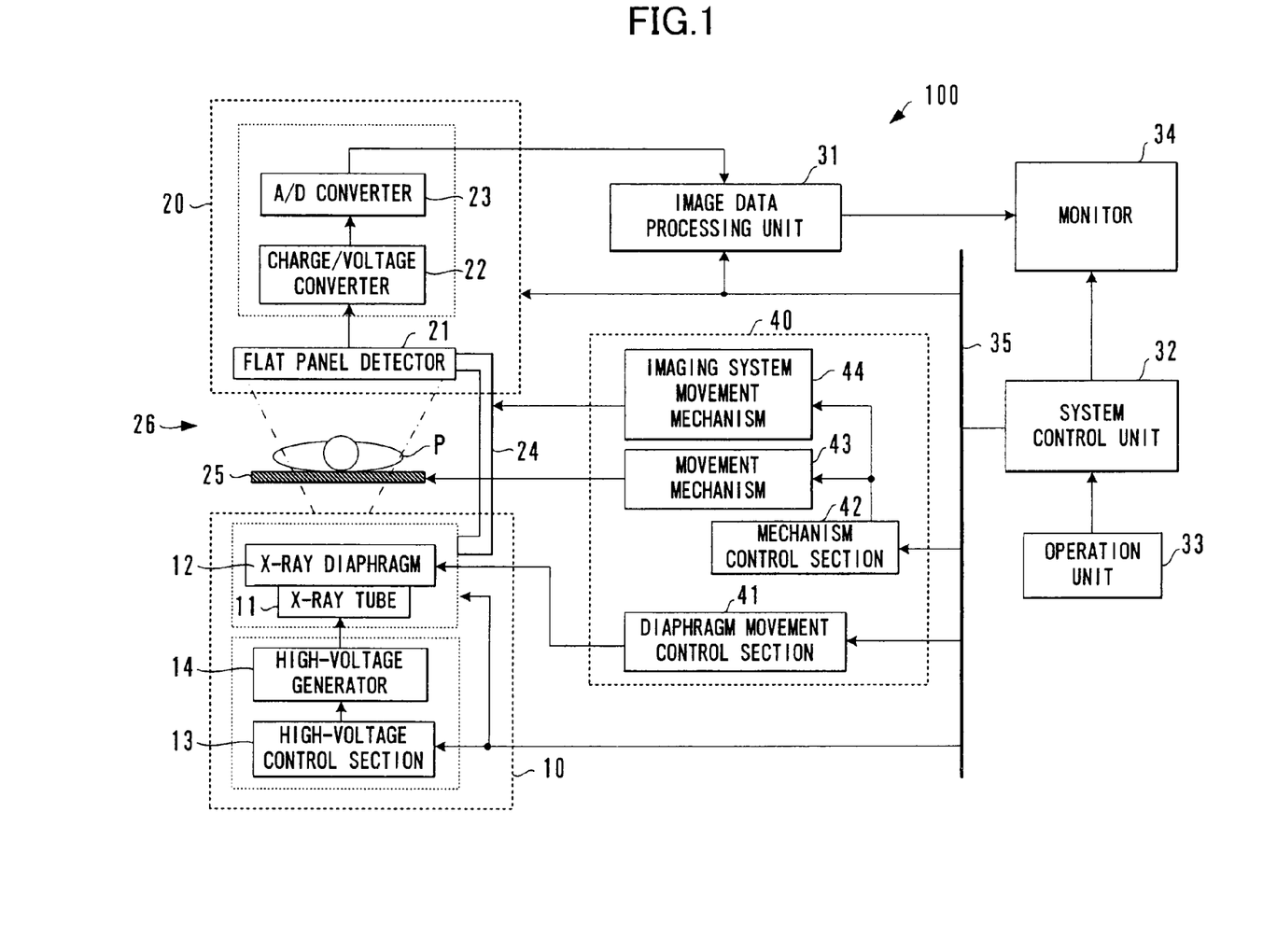
FIG. 1 is a block diagram showing a configuration of an X-ray image diagnosis apparatus according to an embodiment of the present invention.

FIG. 1 is a block diagram showing a configuration of an X-ray image diagnosis apparatus (angiographic apparatus) according to an embodiment of the present invention.

In FIG. 1, an X-ray image diagnosis apparatus 100 includes an X-ray generation unit 10 that generates X-ray to be irradiated onto a subject P and an X-ray detection unit 20 that two-dimensionally detects X-ray transmitted through the subject P and generates X-ray projection data based on a result of the detection.

The X-ray generator 10 includes an X-ray irradiation unit and a high-voltage generation unit. The X-ray irradiation unit has an X-ray tube 11 and an X-ray diaphragm 12. The high-voltage generation unit has a high-voltage control section 13 and a high-voltage generator 14. The X-ray tube 11 is a vacuum tube that produces X-rays. In the X-ray tube 11, electrons released from a filament are accelerated by a high voltage to collide with a tungsten anode for X-ray generation.

The X-ray detection unit 20 includes a flat panel detector 21, a charge/voltage converter 22 that converts a charge read out from the flat panel detector 21 into a voltage, and an A/D converter 23 that converts an output from the charge/voltage converter 22 into a digital signal and outputs X-ray projection data from the A/D converter 23.

The X-ray generation unit 10 and X-ray detection unit 20 are supported by a C-arm 24. The C-arm 24 can be moved in the body axis direction of the subject P placed on a tabletop 25 of a bed and can be rotated around the body axis of the same. The X-ray generation unit 10 and X-ray detection unit 20 constitute an imaging unit 26. The imaging unit 26 is rotated around the subject P along with rotation of the C-arm 24, thereby imaging the subject P from different angle directions.

The X-ray image diagnosis apparatus 100 further includes an image data processing unit 31, a system control unit 32, an operation unit 33, and a monitor 34. The image data processing unit 31 performs reconstruction processing based on the X-ray projection data from the A/D converter 23 and stores the reconstructed image data. The image data generated in the image data processing unit 31 is displayed on the monitor 34.

The system control unit 32 performs overall control for the respective units in the X-ray image diagnosis apparatus 100 through a bus line 35. The operation unit 33 is used for a user such as a doctor, etc., to input various commands and has an interactive interface provided with an input device such as a mouse, a keyboard, a trackball, and a joystick, a display panel, or various switches.

The X-ray image diagnosis apparatus 100 further includes a movement mechanism unit 40. The movement mechanism unit 40 includes a diaphragm movement control section 41 and a mechanism control section 42. The diaphragm movement control section 41 controls the movement of a diaphragm blade, etc. of the X-ray diaphragm 12, and the mechanism control section 42 controls the movement of a movement mechanism 43 of the tabletop 25 on which the subject P is placed or movement of an imaging system movement mechanism 44. The movement mechanism unit 40 operates in response to operation of the operation unit 33 and performs the movement control for the respective units under the control of the system control unit 32.

Figure 2:
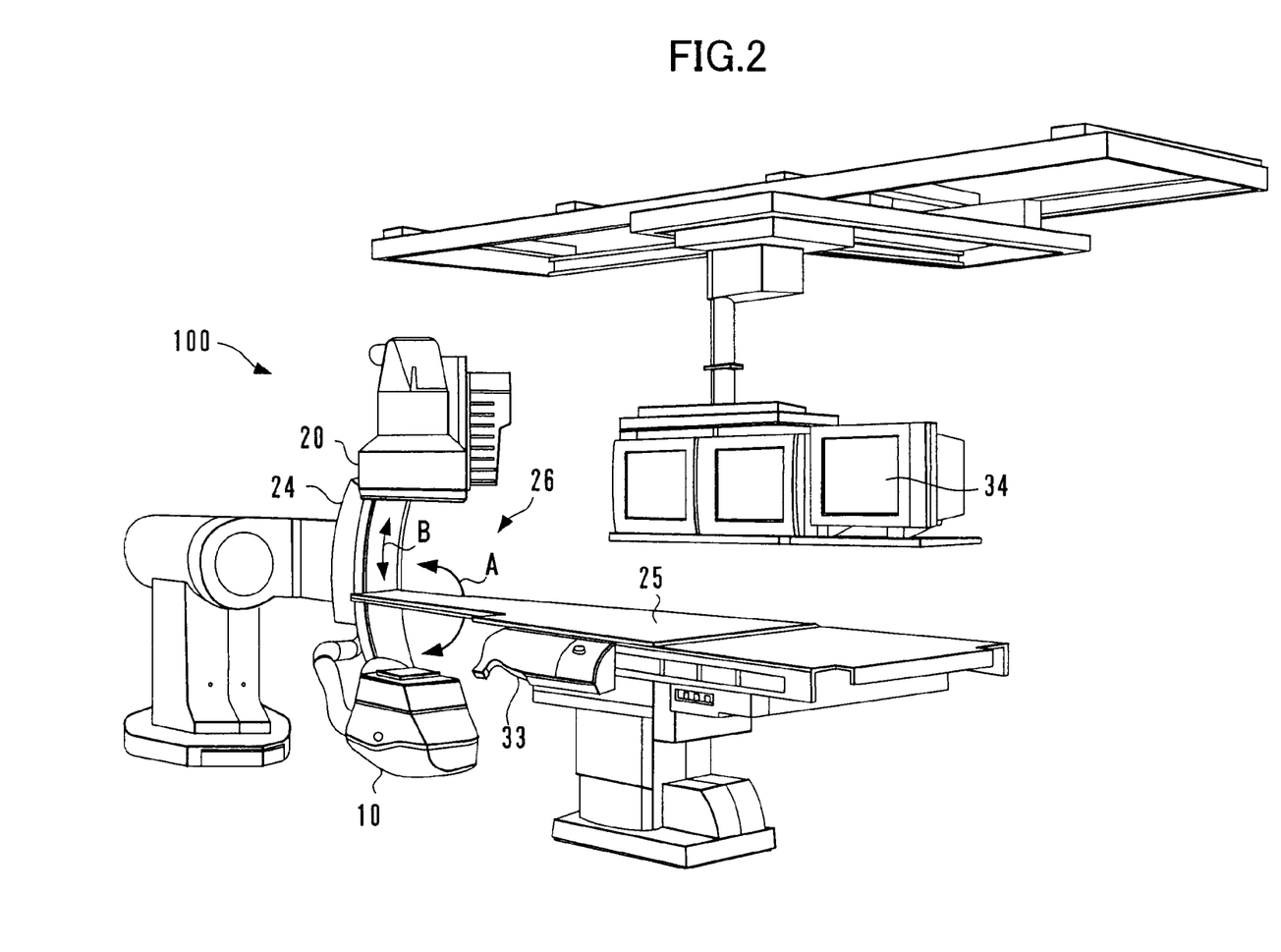
FIG. 2 is a perspective view showing the entire configuration of the X-ray image diagnosis apparatus according to the present embodiment.

FIG. 2 is a perspective view showing the entire configuration of the X-ray image diagnosis apparatus 100 (angiographic apparatus). In the X-ray image diagnosis apparatus 100, the X-ray generator 10 and X-ray detector 20 are supported by the C-arm 24 such that the X-ray generator 10 and X-ray detector 20 are opposed to each other. A bed is disposed to extend toward the C-arm 24. A subject (not shown) is placed on the tabletop 25 of the bed. The horizontal and vertical positions of the tabletop 25 can be controlled by the mechanism control section 42.

The C-arm 24 can be moved in the cranial/caudal direction along the body axis of the subject. Further, as denoted by an arrow A, the imaging unit 26 (X-ray generator 10 and X-ray detector 20) can be rotated in the left/right direction (LAO/RAO direction) around the subject by rotation of the C-arm 24. Further, the imaging unit 26 can be slidably rotated in the direction denoted by an arrow B.

The X-ray projection data is subjected to reconstruction processing by the image data processing unit 31, and reconstructed image data is displayed on the monitor 34. The monitor 34 is fixed to, e.g., a ceiling. The operation unit 33 is mounted in the bed, and the system control unit 32 performs control of the vertical position of the tabletop 25, control of movement/rotation of the C-arm 24, adjustment of X-ray irradiation range, setting of irradiation timing, and the like in response to operation of the operation unit 33.

Figure 3:
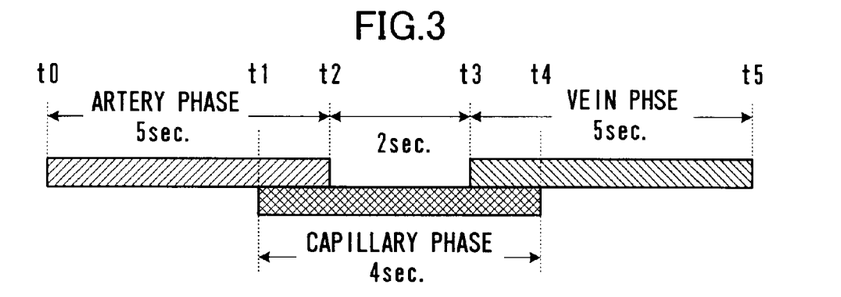
FIG. 3 is an explanatory view showing a temporal change concerning the flow of blood containing contrast medium that flows from the artery to capillaries and further to the vein.

Next, operation of generating a 3D image of the capillary phase performed by the X-ray image diagnosis apparatus 100 according to the present invention will be described. FIG. 3 shows a temporal change concerning blood flow observed in angiographic examination in which contrast medium is injected into the artery and blood containing contrast medium flows from the artery to capillaries and further to the vein.

As shown in FIG. 3, upon injection of the contrast medium into the artery at timing t0, blood containing contrast medium flows in the artery for about 5 seconds from timing t0 to timing t2. At about timing t1, the blood is pumped from the artery to capillaries and flows in the capillaries for about 4 seconds from timing t1 to timing t4. Then, at about timing t3, the blood is pumped from the capillaries to the vein and flows in the vein for about 5 seconds from timing t3 to timing t5.

Figure 4A:
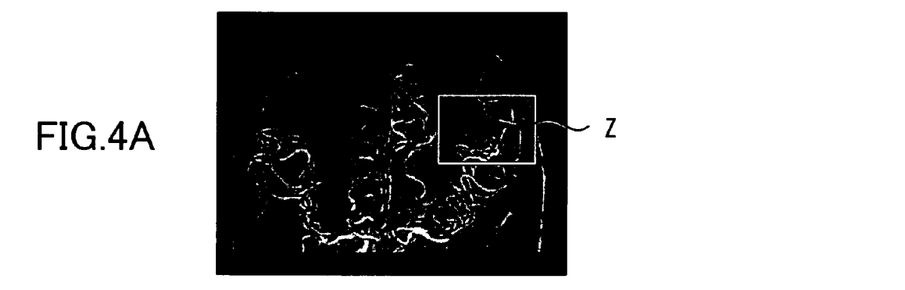
FIGS. 4A to 4C are explanatory views showing examples of images representing states where blood containing contrast medium flows in the artery, capillaries, and vein.
Figure 4B:
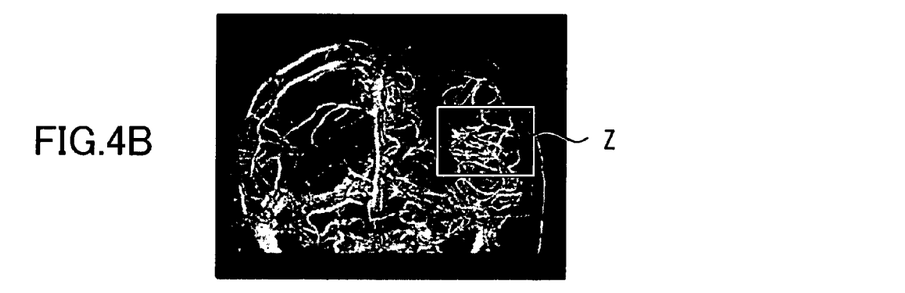
Figure 4C:
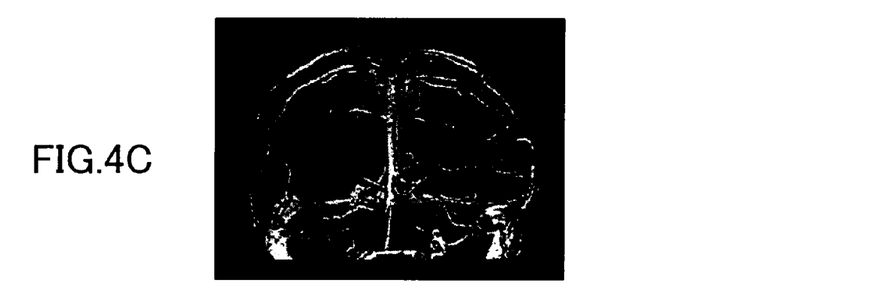

FIGS. 4A to 4C each show an example of an image representing a state where the blood containing contrast medium flows from the artery to capillaries and further to the vein. FIG. 4A shows a vessel image in the artery phase, FIG. 4B shows a vessel image in the capillary phase, and FIG. 4C shows a vessel image in the vein phase.

However, as described above with reference to FIG. 3, the blood containing contrast medium exists in both the artery and capillaries from timing t1 to timing t2, and blood containing contrast medium exists in both the capillaries and vein from timing t3 to timing t4. Further, a time period during which the blood containing contrast medium exists mainly in the capillaries is very short (about 2 seconds) as denoted by the time period from timing t2 to timing t3 of FIG. 3.

As described above, only about 4 seconds can be used for imaging the blood vessel in the capillary phase. In 3D angiography, it is possible to obtain a 3D reconstruction image by performing imaging with the imaging unit 26 rotated by 180 or more degrees. However, in order to generate a 3D image, the imaging unit 26 needs to be rotated within an angular range of about 200 degrees.

That is, the imaging unit 26 needs to be rotated by about 50 degrees per one second. However, in existing systems, it is impossible to rotate the imaging unit by 200 degrees within a time period (time period of t2 to t3: about 2 seconds) during which the blood containing contrast medium flows in the capillaries. Under existing circumstances, the imaging unit can be rotated by 200 degrees per 4 seconds at most. Therefore, an obtained capillary image includes an image of the artery or vein.

In the embodiment of the present invention, when an image of the subject P of a predetermined angular range (e.g., 200 degrees) required for 3D image reconstruction is obtained through imaging with the imaging unit 26 rotated about the body axis of the subject P, the imaging unit 26 is rotated within a first angular range and then within a second angular range to perform a first imaging operation and a second imaging operation, respectively, such that images in the first and second angular ranges partly are overlapped with each other.

That is, 3D imaging operation is performed two times in such a manner that the first imaging operation is performed within a rotation range of about 120 degrees and second imaging operation is performed within a rotation range of about 120 degrees from a different direction. Further, the imaging range is defined so that an overlap area is generated by the first and second imaging operations.

Imaging is discretely performed for a range unnecessary for 3D image reconstruction, only the images of the capillary phase are extracted from the images obtained through the two imaging operations, and the artery and vein phases are separated from the images corresponding to the overlap area. Further, there is a possibility that a displacement may occur between the images obtained by the first and second imaging operations due to movement of a patient, so that the images obtained by the first and second imaging operations are compared with each other using an image of bones or blood vessels obtained by the two imaging operations so as to compensate the displacement (body movement). Thus, 200-degree imaging operation can be achieved in 2 seconds (two times).

The rotation of the imaging unit 26 and X-ray irradiation timing are controlled by the system control unit 32, and image processing including reconstruction of the image data obtained through imaging, motion compensation, and the like is performed by the image data processing unit 31 under the control of the system control unit 32.

In the reconstruction processing, images obtained through imaging performed in different directions are subjected to back-projection processing and thereby a cross-unital image or 3D image data representing the tissue structure inside the subject is obtained.

Operation of correcting the capillary image will concretely be described with reference to FIGS. 5A to 5E. In the following description, the term "injection" denotes injection of the contrast medium, and "artery phase", "vein phase", and "capillary phase" denote the phase in which the contrast medium is flowing in the artery, phase in which the contrast medium is flowing in the vein, and phase in which the contrast medium is flowing in the capillaries, respectively.

Figure 5A:
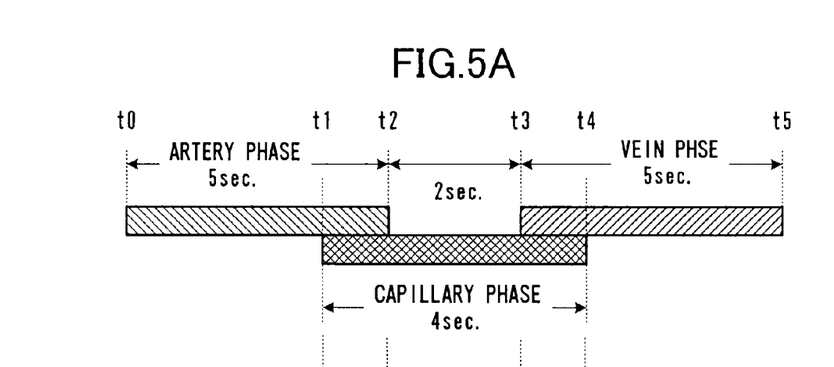
FIGS. 5A to 5E are explanatory views showing imaging operation for obtaining contrast image data.

FIGS. 5A to 5E show the entire imaging operation for obtaining contrast image data with a use of the contrast medium. FIG. 5A shows a temporal change concerning blood flow observed when the contrast medium is injected into the artery and blood containing contrast medium flows from the artery to capillaries and further to the vein. A first imaging operation is performed from timing t1 to timing t3, and a second imaging operation is performed from timing t2 to timing t4.

Figure 5B:
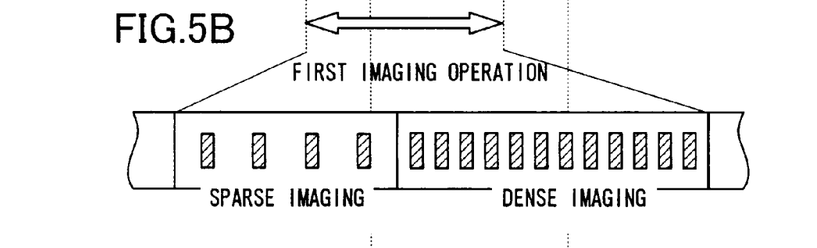

FIG. 5B shows, in an enlarged manner, the period during which the first imaging operation is performed. That is, in a predetermined time period starting from the start of the imaging, imaging is performed discretely with the imaging interval set large, and, after elapse of the predetermined time period, imaging is performed densely with the imaging interval set small. Image data obtained through the discrete imaging (sparse imaging) is used for motion compensation, and image data obtained by the dense imaging is used for image reconstruction. Shaded areas in FIG. 5B each denote the imaging timing.

Figure 5C:
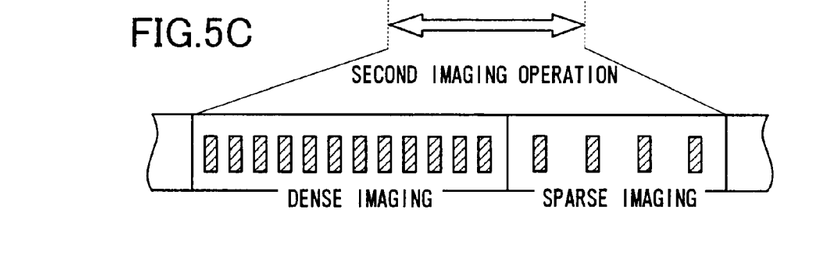
Figure 5D:
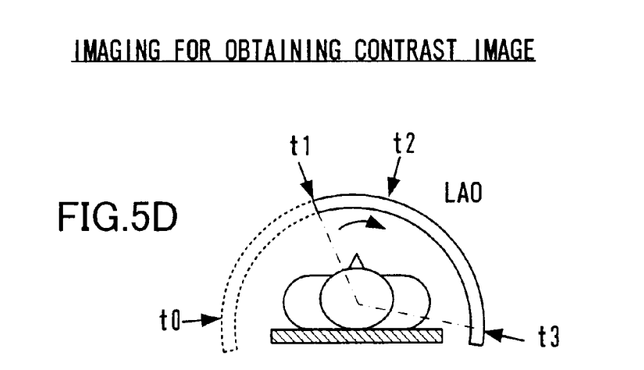

FIG. 5D shows the rotation operation of the imaging unit 26 at the time of the first imaging operation. In FIG. 5D, assuming that the contrast medium is injected at timing t0, the imaging unit 26 starts its rotation at timing t0 and starts irradiation of X-ray at the time point (at timing t1) when a predetermined time (about 4 seconds) has elapsed.

While being rotated, the imaging unit 26 performs the sparse imaging from timing t1 to timing t2 and performs the dense imaging after timing t2 as shown in FIG. 5B. At timing t3, the imaging unit 26 stops the rotation and ends the imaging operation. That is, the imaging is actually performed while the imaging unit 26 is rotated by about 120 degrees within a time period from timing t1 to timing t3, i.e., at the timing at which the blood containing contrast medium flows from the artery to capillaries. In particular, at the timing at which the blood containing contrast medium flows in the capillary phase, the dense imaging is performed.

FIG. 5C shows, in an enlarged manner, the period during which the second imaging operation is performed. In this operation, the imaging unit 26 is rotated in the direction opposite to the rotation direction in the first imaging operation (see FIG. 5E). In a predetermined time period starting from the start of the imaging, the imaging is performed densely with the imaging interval set small, and, after elapse of the predetermined time period, imaging is performed discretely with the imaging interval set large. Image data obtained by the dense imaging is used for image reconstruction, and image data obtained through the discrete imaging (sparse imaging) is used for motion compensation.

Figure 5E:
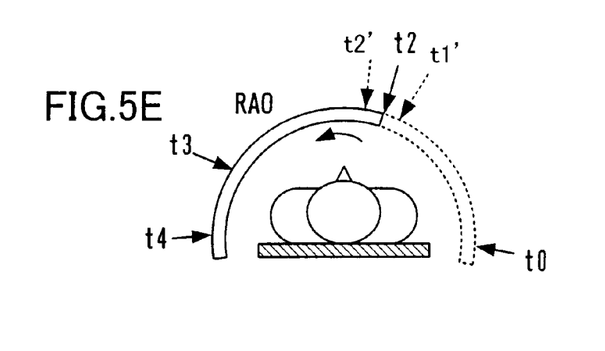

FIG. 5E shows the rotation operation of the imaging unit 26 at the time of the second imaging operation. In FIG. 5E, assuming that the contrast medium is injected at timing t0, the imaging unit 26 starts its rotation at timing t0 and starts irradiation of X-ray at the time point (at timing t2) when a predetermined time (about 5 seconds) has elapsed.

While being rotated, the imaging unit 26 performs the dense imaging from timing t2 to timing t3 and performs the sparse imaging after timing t3. At timing t4, the imaging unit 26 stops the rotation and ends the imaging operation. That is, the imaging is actually performed while the imaging unit 26 is rotated by about 120 degrees within a time period from timing t2 to timing t4, i.e., at the timing at which the blood containing contrast medium flows from the capillaries to vein. In particular, at the timing at which the blood containing contrast medium flows in the capillary phase, the dense imaging is performed.

As shown in FIGS. 5B and 5C, the two imaging operations each cover an angular range (e.g., 120 degrees) larger than 100 degrees including the area to be overlapped. Thus, by synthesizing the image data obtained through the two imaging operations, it is possible to obtain an image covering an angular range of about 200 degrees required for reconstructing a 3D image.

In the first imaging operation, the time length from the start of the injection to X-ray irradiation is set based on fluoroscopy performed before the imaging, analysis information before treatment, and the like. Further, the boundary between the artery phase and capillary phase, or boundary between the capillary phase and vein phase can be determined by a human operator or through software processing based on blood concentration containing contrast medium. Accordingly, in the second imaging operation, X-ray irradiation start timing may be changed as needed based on the number of seconds taken for the phase to be shifted from the artery phase to capillary phase in the first imaging operation.

For example, an area Z in which a large number of capillaries exist is set as shown in FIG. 4A, and a state where the blood containing contrast medium flows during the first imaging operation is analyzed. When the phase is shifted from the artery phase to capillary phase, the blood flow in the capillary phase starts to increase, so that the timing at which the blood concentration in the area Z exceeds a predetermined threshold is determined as the timing at which the phase is shifted from the artery phase to capillary phase.

Thus, in the second imaging operation, X-ray irradiation may be started based on information obtained by analyzing the result of the first imaging operation, i.e., data indicating the timing at which the phase is shifted from the artery phase to capillary phase. Thus, as denoted by t1' or t2' of FIG. 5E, X-ray irradiation start timing can be changed in accordance with the current condition of the subject. The system control unit 32 constitutes a timing setting unit for setting X-ray irradiation start timing. Alternatively, a doctor himself or herself, etc., may set the X-ray irradiation start timing.

Figure 6A:
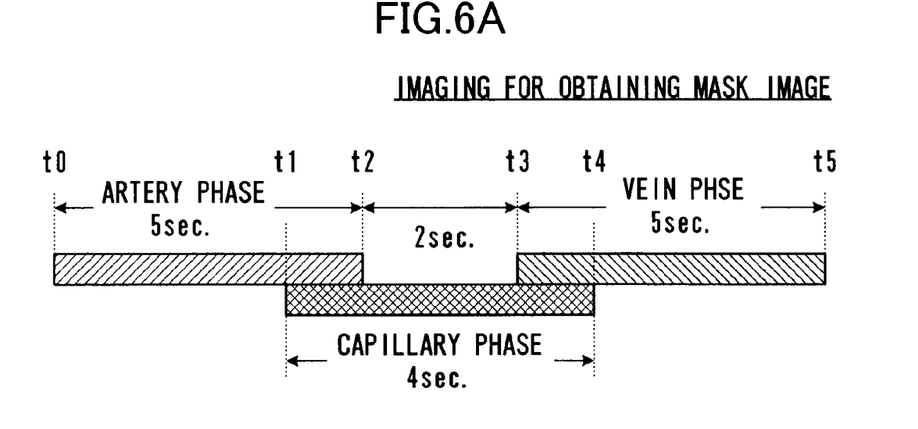
FIGS. 6A and 6B are explanatory views showing imaging operation for obtaining mask image data.
Figure 6B:
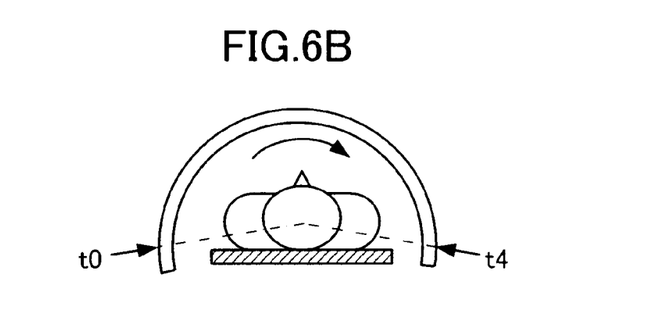

FIGS. 6A and 6B show an imaging operation for obtaining mask image data. The imaging for obtaining the mask image is performed before the injection of the contrast medium into blood vessels. FIG. 6A shows the blood flowing from the artery to capillaries and further to the vein. As shown in FIG. 6B, in the imaging operation for obtaining the mask image, an angular range of 200 degrees is covered by a single imaging operation. The imaging unit 26 starts its rotation at, e.g., timing t1 to irradiate X-ray and stops the rotation at timing t4 to stop the imaging operation. The imaging operation for obtaining the mask image is performed without use of the contrast medium, and the obtained mask image does not include an image of the blood vessels.

In the manner as described above, the contrast image data and mask image data can be obtained through the imaging that covers an angular range of about 200 degrees required for 3D image reconstruction. The contrast image data obtained through the two imaging operations are then subjected to motion compensation, reconstruction, and synthesis processing, whereby a 3D image can be displayed on the monitor 34.

The first and second imaging operations for obtaining the contrast image each covering an angular range of about 120 degrees are performed from different angular directions, it is necessary to analyze whether images of an area appropriated for 3D image reconstruction of the capillary phase have been extracted. Thus, the mask image and contrast image are subjected to subtraction processing to thereby obtain a subtraction image, and whether an image of the capillary phase has been extracted is analyzed based on the subtraction image.

The motion compensation is a technique for compensating a displacement occurring between the contrast images obtained by the first and second imaging operations. In the motion compensation, based on an image of bones or angiographic image obtained through the first and second imaging operations, a displacement occurring between subject images obtained through the first and second imaging operations is compensated. That is, there may be a case where the position or inclined angle of the subject in the second imaging operation is slightly from that in the first imaging operation, so that the position or angle of one of the images obtained through the first and second imaging operations is compensated based on the displacement amount between the images of the first and second imaging operations. An image for the motion compensation is obtained through the sparse imaging, leading to a reduction of radiation exposure to the subject.

Further, there is a possibility that the artery phase and capillary phase may exist in a mixed manner in the image obtained through the first imaging operation, and there is a possibility that the capillary phase and vein phase exist in a mixed manner in the image obtained through the second imaging operation. Thus, the images of the first and second imaging operations are compared so as to extract only a portion that exists commonly in both the two images, whereby the artery phase and vein phase can be separated from the capillary phase. As a result, it is possible to extract an image of the capillary phase for reconstruction. In this manner, the images obtained through the two imaging operations are then subjected to reconstruction processing and then to synthesis processing, whereby an image of the capillary phase can be displayed in a 3D manner.

Figure 7:
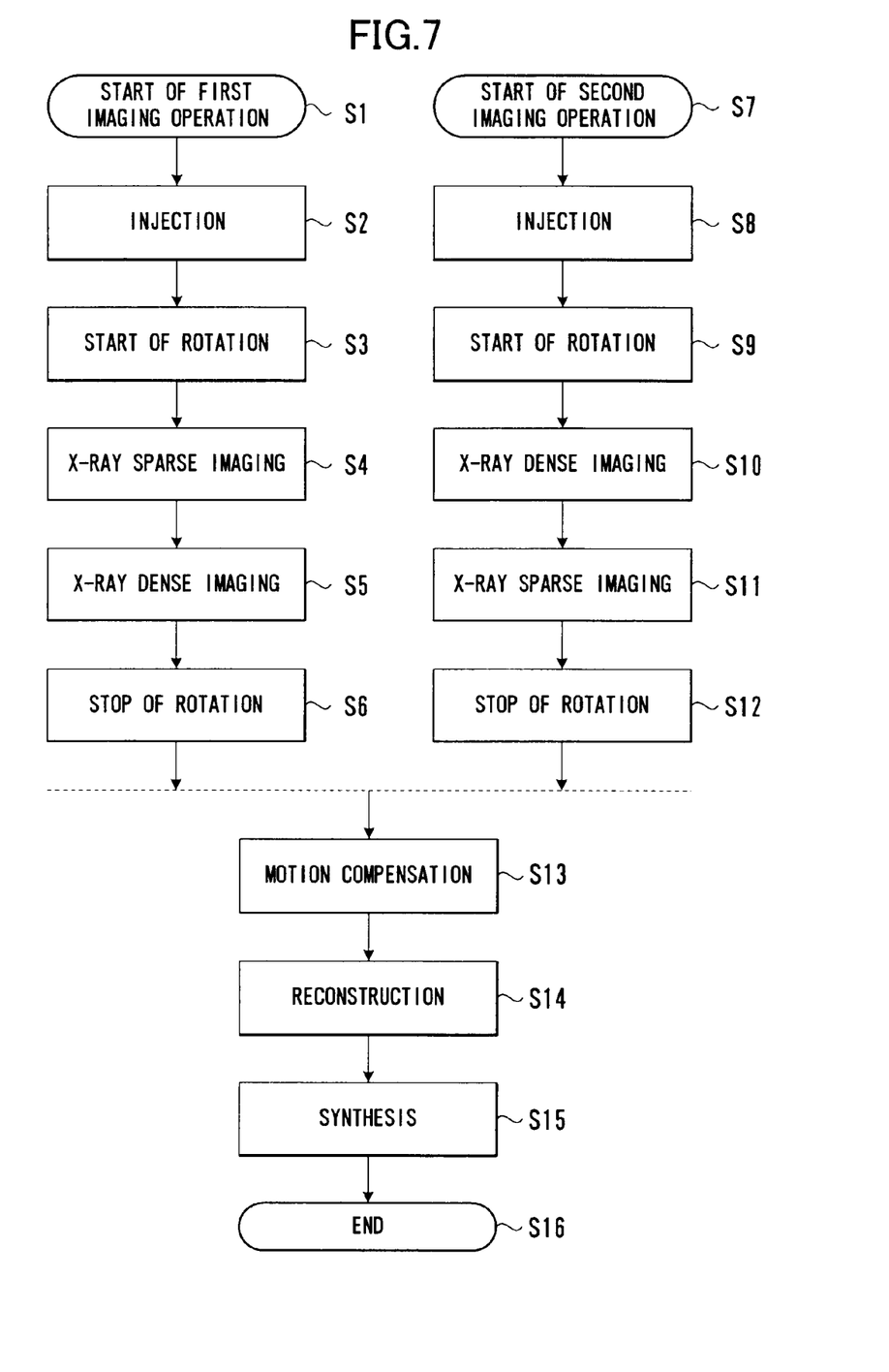
FIG. 7 is a flowchart showing a procedure from collection of the contrast image to synthesis processing.

FIG. 7 is a flowchart showing a procedure from collection of the contrast image to synthesis of the images obtained through the first and second imaging operations. In FIG. 7, step S1 is a first imaging operation start step, and injection is performed in step S2. In step S3, the imaging unit 26 starts its rotation. After the imaging unit 26 is rotated by a predetermined angle, X-ray sparse imaging is performed in step S4. After the imaging unit 26 is further rotated, X-ray dense imaging is performed in step S5. Then, after the imaging unit 26 is further rotated up to a predetermined angular position, it stops the rotation in step s6 and ends the first imaging operation.

Step S7 is a second imaging operation start step, and injection is performed in step S8. In step S9, the imaging unit 26 starts its rotation in the direction opposite to the rotation direction in the first imaging operation. After the imaging unit 26 is rotated by a predetermined angle, X-ray dense imaging is performed in step S10. After the imaging unit 26 is further rotated, X-ray sparse imaging is performed in step S11. Then, after the imaging unit 26 is further rotated up to a predetermined angular position, it stops the rotation in step S12 and ends the second imaging operation.

After completion of the two imaging operations, a displacement occurring between subject images obtained through the first and second imaging operations is analyzed to perform motion compensation in step S13 based on an image of bones or angiographic image obtained through the first and second imaging operations. Then, in step S14, reconstruction processing is performed based on the motion-compensated image data. That is, only images of the capillary phase that exist commonly among the images obtained through the first and second imaging operations are extracted and then reconstructed.

In step S15, the reconstructed images are synthesized to generate a 3D image of the capillary phase, and the flow is ended in step S16.

Figure 8:
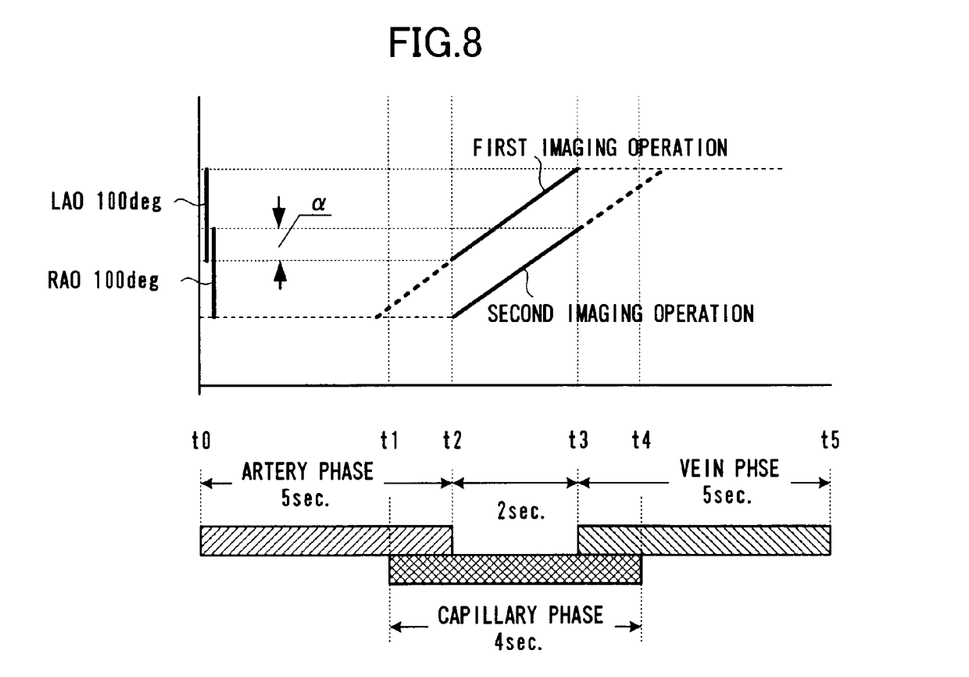
FIG. 8 is an explanatory view showing operation for collecting the capillary images.

FIG. 8 is another explanatory view showing the operation for collecting the capillary images. In FIG. 8, time is plotted on the horizontal axis, and a temporal change concerning the flow of blood containing contrast medium that flows from the artery to capillaries and further to the vein is shown when the contrast medium is injected into the artery.

The vertical axis represents the imaging range (angle) of the imaging unit 26. The first imaging operation is performed from timing t1 to timing t3 during which the imaging unit 26 is rotated. In the first imaging operation, the sparse imaging is performed from timing t1 to timing t2, and dense imaging is performed from timing t2 to timing t3. At timing t3, the imaging unit 26 stops its rotation and ends the first imaging operation.

The second imaging operation is performed from timing t2 to timing t4 during which the imaging unit 26 is rotated. In the second imaging operation, the dense imaging is performed from timing t2 to timing t3, and sparse imaging is performed from timing t3 to timing t4. At timing t4, the imaging unit 26 stops its rotation and ends the second imaging operation.

LAO 100 deg. denotes the imaging range (about 100 degrees) in the first dense imaging, RAO 100 deg. denotes the imaging range (about 100 degrees) in the second dense imaging, and angle range $\alpha$ denotes an overlap area between image areas obtained through the first and second dense imaging.

In the above description, the imaging unit 26 is rotated in a first direction in the first imaging operation and it is rotated in a second direction opposite to the first direction in the second imaging operation. Alternatively, however, the imaging unit 26 may be rotated in the manner as shown in FIGS. 9A and 9B.

Figures 9A, 9B:
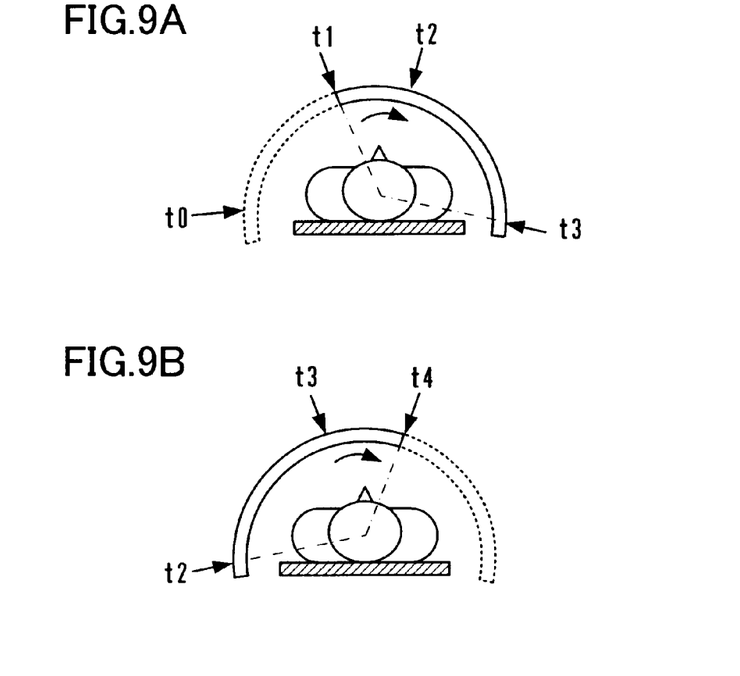
FIGS. 9A and 9B are explanatory views showing another example of rotation operation of the imaging unit.

FIG. 9A shows the rotation operation of the imaging unit 26 in the first imaging operation.

That is, the imaging unit 26 starts its rotation at timing t0 after the injection and starts irradiation of X-ray at the time point (at timing t1) when a predetermined time (about 4 seconds) has elapsed. While being rotated, the imaging unit 26 performs the sparse imaging from timing t1 to timing t2 and performs the dense imaging after timing t2. At timing t3, the imaging unit 26 stops the rotation and ends the imaging operation.

For the second imaging operation, the imaging unit 26 is set back to its original position as shown in FIG. 9B. Then, the imaging unit 26 starts its rotation in the same direction as in FIG. 9A at the time point when a predetermined time (about 5 seconds) has elapsed from timing t0 of the injection timing and starts irradiation of X-ray at timing t2. While being rotated, the imaging unit 26 performs the dense imaging from timing t2 to timing t3 and performs the sparse imaging after timing t3. At timing t4, the imaging unit 26 stops the rotation and ends the imaging operation.

Thus, the first imaging operation is performed while the imaging unit 26 is rotated by about 120 degrees from an angular position to which the imaging unit 26 has been rotated by a predetermined angle, and second imaging operation is performed while the imaging unit 26 is rotated by about 120 degrees from the start of its rotation. In this case, the imaging areas of the first and second imaging operations are overlapped in the vicinity of an angular position at which the first imaging operation is started and second imaging operation is ended.

In the above description, the motion compensation is performed after completion of the two imaging operations and then the reconstruction processing is performed. Alternatively, however, a procedure may be adopted in which the reconstruction processing is performed after completion of the two imaging operations and then the motion compensation is performed.

As described above, in the present invention, imaging images can be collected over an angular range of about 200 degrees by two imaging operations, and by performing 3D reconstruction using images of only the capillary phase, artifacts can be reduced. Further, even if the subject moves to generate a displacement between the images obtained though the first and second imaging operations, the displacement can be compensated by motion compensation.

Thus, it is possible to obtain a 3D image only including the capillary phase in the angiographic apparatus. Further, the 3D image can be obtained even immediately after endovascular treatment, so that a blood clot can be found timely. If the blood clot is found, treatment can be applied once again immediately. Thus, the blood flow in the capillary phase can be diagnosed correctly.

The embodiment of the present invention is not limited to the above description but may be variously modified within the scope of the invention as defined in the claims.

Additional advantages and modifications will readily occur to those skilled in the art. Therefore, the invention in its broader aspects is not limited to the specific details and representative embodiment shown and described herein. Accordingly, various modifications may be made without departing from the spirit or scope of the general inventive concept as defined by the appended claims and their equivalents.

What is claimed is:

1. An X-ray image diagnosis apparatus comprising:
   an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed;
   a control unit that rotates, after injection of contrast medium into the subject, the imaging unit about the body axis of the subject to perform imaging for obtaining images within a predetermined angular range required for image reconstruction, the control unit rotating the imaging unit within a first angular range to perform a first imaging operation and then rotating the imaging unit within a second angular range to perform a second imaging operation, and performs overlapped dense imaging for a phase in which blood containing the contrast medium flows in capillaries as an area to be reconstructed, and performs sparse imaging for a phase in which blood containing the contrast medium flows from the artery to capillaries and from the capillaries to a vein; and
   an image data processing unit that performs image reconstruction processing based on two images obtained through the first and second dense imaging operations after compensating a displacement occurring between the images obtained by the first and second imaging operations.

2. The X-ray image diagnosis apparatus according to claim 1, wherein,
   the image data processing unit uses the images obtained through the sparse imaging to compensate a displacement occurring between the images obtained by the two imaging operations.

3. The X-ray image diagnosis apparatus according to claim 1, wherein,
   in the first and second imaging operations, the control unit sets the rotation start time of the imaging unit and time that elapses before the start of imaging based on the time length from the injection of the contrast medium to the time at which blood containing the contrast medium reaches the capillaries.

4. An X-ray image diagnosis apparatus comprising:
   an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed;
   a control unit that rotates, after injection of contrast medium into the subject, the imaging unit about the body axis of the subject to perform imaging for obtaining images within a predetermined angular range required for image reconstruction, the control unit rotating the imaging unit within a first angular range to perform a first imaging operation and then rotating the imaging unit within a second angular range to perform a second imaging operation, and performs overlapped dense imaging for a phase in which blood containing the contrast medium flows in capillaries as an area to be reconstructed, and performs sparse imaging for a phase in which blood containing the contrast medium flows from the artery to capillaries and from the capillaries to a vein;
   a timing setting unit that analyzes the time length from the injection of the contrast medium to the time at which blood containing the contrast medium reaches the capillaries based on the result of the first imaging operation and sets the X-ray irradiation start time in the second imaging operation based on the analysis result; and
   an image data processing unit that performs image reconstruction processing based on two images obtained through the first and second dense imaging operations.

5. An X-ray image processing method comprising:
   providing an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed;
   rotating the imaging unit within a first angular range after injection of contrast medium into the subject to perform a first imaging operation at imaging time in which the imaging unit is rotated about the body axis of the subject to perform imaging for obtaining images within a predetermined angular range required for image reconstruction, and performs sparse imaging for a phase in which blood containing the contrast medium flows from the artery to capillaries and performs dense imaging for a phase in which blood containing the contrast medium flows in capillaries as an area to be reconstructed;
   rotating the imaging unit within a second angular range after injection of contrast medium into the subject to perform a second imaging operation such that a part of the first angular range and a part of the second angular range are overlapped with each other, and performs dense imaging for a phase in which blood containing the contrast medium flows in capillaries as an area to be reconstructed and performs sparse imaging for a phase in which blood containing the contrast medium flows from the capillaries to a vein; and performing image reconstruction processing based on two images obtained through the first and second dense imaging operations after compensating a displacement occurring between the images obtained by the first and second sparse imaging operations.

6. An X-ray image processing method comprising:

providing an imaging unit that includes an X-ray generation unit for irradiating X-ray onto a subject and an X-ray detection unit for detecting X-ray transmitted through the subject, which are supported so as to be opposed to each other and rotatable about the body axis of the subject placed on a bed;

rotating the imaging unit within a first angular range after injection of contrast medium into the subject to perform a first imaging operation at imaging time in which the imaging unit is rotated about the body axis of the subject to perform imaging for obtaining images within a predetermined angular range required for image reconstruction, and performs sparse imaging for a phase in which blood containing the contrast medium flows from the artery to capillaries and performs dense imaging for a phase in which blood containing the contrast medium flows in capillaries as an area to be reconstructed;

analyzing the time length from the injection of the contrast medium to the time at which blood containing the contrast medium reaches the capillaries based on the result of the first imaging operation;

setting the X-ray irradiation start time in the second imaging operation based on the analysis result;

rotating the imaging unit within a second angular range after injection of contrast medium into the subject to perform a second imaging operation such that a part of the first angular range and a part of the second angular range are overlapped with each other, and performs dense imaging for a phase in which blood containing the contrast medium flows in capillaries as an area to be reconstructed and performs sparse imaging for a phase in which blood containing the contrast medium flows from the capillaries to a vein; and performing image reconstruction processing based on two images obtained through the first and second dense imaging operations.

* * * * *